(12) United States Patent
Ott

(10) Patent No.: US 10,330,575 B2
(45) Date of Patent: Jun. 25, 2019

(54) APPARATUS AND METHOD FOR ATTACHING AND TESTING A SLEEVE WITH A COUPLING END TO A STEEL WIRE

(71) Applicant: Wireteknik AB, Stockholm (SE)

(72) Inventor: Jesper Ott, Nacka Strand (SE)

(73) Assignee: Wireteknik AB, Stockholm (SE)

( * ) Notice: Subject to any disclaimer, the term of this patent is extended or adjusted under 35 U.S.C. 154(b) by 0 days.

(21) Appl. No.: 15/496,306

(22) Filed: Apr. 25, 2017

(65) Prior Publication Data
US 2017/0307492 A1    Oct. 26, 2017

(30) Foreign Application Priority Data

Apr. 26, 2016 (EP) ..................................... 16167100

(51) Int. Cl.
*F16G 11/02*    (2006.01)
*D07B 9/00*    (2006.01)
(Continued)

(52) U.S. Cl.
CPC .............. *G01N 3/10* (2013.01); *B21F 15/00* (2013.01); *B21H 1/22* (2013.01); *B23P 11/005* (2013.01); *B23P 19/047* (2013.01); *F16G 11/025* (2013.01); *D07B 7/027* (2013.01); *D07B 9/00* (2013.01)

(58) Field of Classification Search
CPC ......... G01N 3/10; B23P 19/047; A63B 61/02; A63B 2071/0694; A63B 2243/0095; A63B 2102/02; A63B 2102/04; A63B 2102/16; A63B 2220/51; G01L 5/103; G01L 5/0028; G01L 5/24
See application file for complete search history.

(56) References Cited

U.S. PATENT DOCUMENTS 3,342,067 A * 9/1967 Bush .......................... G01L 5/06
                                                              73/158
3,620,071 A * 11/1971 Kelley et al. .......... G01B 17/04
                                                              73/159
(Continued)

FOREIGN PATENT DOCUMENTS

| GB | 602963 A | 6/1948 |
|---|---|---|
| GB | 2 062 519 A | 5/1981 |
| GB | 2 053 760 B | 2/1983 |

*Primary Examiner* — Harshad R Patel
*Assistant Examiner* — Brandi N Hopkins
(74) *Attorney, Agent, or Firm* — Blank Rome LLP

(57) ABSTRACT

Apparatus for attaching a sleeve comprising a coupling end to a steel wire. The apparatus comprises a pulling end arranged to connect to a sleeve to be attached to a steel wire, a pulling arrangement connected to the pulling end and being configured to pull a sleeve connected to the pulling end, a swaging arrangement comprising two opposed swaging rolls adapted to crimp the sleeve to a close press fit around a loose end of a steel wire. The apparatus further comprises a testing arrangement for testing the strain capacity of the attachment of a sleeve to a steel wire, the testing arrangement including a holding unit configured to effectively hold a portion of the steel wire fixed and allowing the pulling arrangement to pull the sleeve attached to a wire held fixed in the holding unit in order to verify the attachment.

10 Claims, 2 Drawing Sheets

(51) Int. Cl.
    *D07B 7/02*     (2006.01)
    *G01N 3/10*     (2006.01)
    *B23P 19/04*     (2006.01)
    *B21F 15/00*     (2006.01)
    *B21H 1/22*     (2006.01)
    *B23P 11/00*     (2006.01)

(56) References Cited

U.S. PATENT DOCUMENTS

| | | | | |
|---|---|---|---|---|
| 3,771,343 A | * | 11/1973 | Dawson | B21D 39/046 |
| | | | | 29/237 |
| 4,000,557 A | * | 1/1977 | Bawden | B21F 15/06 |
| | | | | 24/115 A |
| 4,318,290 A | * | 3/1982 | Anderson | D07B 7/16 |
| | | | | 29/517 |
| 5,351,553 A | * | 10/1994 | Lepie | G01N 3/31 |
| | | | | 73/806 |

\* cited by examiner

APPARATUS AND METHOD FOR ATTACHING AND TESTING A SLEEVE WITH A COUPLING END TO A STEEL WIRE

TECHNICAL FIELD

The invention relates to an apparatus for attaching a sleeve to a steel wire or the like by swaging. Specifically, the invention relates to such an apparatus that is also adapted to test and verify the attachment of the sleeve to said steel wire.

BACKGROUND

Steel wires are used in a wide variety of applications and often a sleeve with a coupling end is attached to at least one end of the steel wire for facilitating handling of the steel wire. Such sleeves are advantageously attached to the steel wire by means of a swaging machine. Different types of swaging machines exist and they may typically be divided in different categories depending on the means for creating the pulling force. Hence, there are inter alia electric apparatuses, combustion driven apparatuses and hydraulic apparatuses.

An advantageous such apparatus is described in GB 2053760 B, in which a pulling arrangement is provided to achieve the needed pulling force. This document describes the background of swaging technique and is hereby inserted by reference.

The swaging technique has proven effective and is widely used. However, in order to guarantee correct attachment of a sleeve to a steel wire over time the wire-sleeve attachment needs to be pull tested up to a specific pull force at specific intervals. Such testing is cumbersome and either necessitates moving of the steel wire to a testing apparatus or installing of a cumbersome testing apparatus on location.

Hence there is a need of an arrangement that facilitates testing of the connection between a sleeve and a steel wire to which it is attached.

SUMMARY OF THE INVENTION

It is an object of the present invention to provide an apparatus that facilitates reliable testing of the connection between a sleeve and a steel wire to which it is attached. A further object is to provide a multifunctional apparatus which is adapted to perform both attachment of a sleeve to a steel wire and testing of said attachment. These objects are achieved by the inventive apparatus as described and claimed herein.

The invention relates to an apparatus for attaching a sleeve comprising a coupling end to a steel wire, the apparatus comprising: an attachment piece arranged to connect to the coupling end of the sleeve to be attached to the steel wire, a pulling arrangement connected to the attachment piece and being configured to pull the sleeve via the connected attachment piece, a swaging arrangement comprising two opposed swaging rolls adapted to crimp the sleeve to a close press fit around a loose end of a steel wire. The apparatus further comprises a testing arrangement for verifying the strain capacity of the attachment of the sleeve to the steel wire, the testing arrangement including a holding unit configured to effectively hold a portion of the steel wire fixed and allowing the pulling arrangement to pull the sleeve attached to the wire held fixed in said holding unit in order to verify said attachment.

The inventive apparatus offers the possibility of attaching and verifying the thus achieved attachment within the same machine. Further, the simplicity of the apparatus and its manageable size makes it possible to bring the apparatus to installations where the fixation of sleeves to steel wires or the like needs to be verified. Further, if needed, fixation of a new sleeve to a steel wire may also be achieved on location.

In a specific embodiment of the inventive apparatus the holding unit comprises two opposed support units with inclined surfaces arranged to support two wedges for holding the steel wire fixed. The wedges may comprise tracks arranged to fit tightly around the steel wire to be fixed. Further, the wedges and/or the tracks of the support units may be provided with a low friction surface layer. Preferably, said low friction surface layer is comprised of a plastic material, such as a polyamide material.

In another specific embodiment the inventive apparatus comprises an indication means for monitoring the traction force applied by the pulling arrangement.

In yet another specific embodiment of the inventive apparatus the swaging rolls may be positioned in an inactive position so as to allow free passage of a wire and a sleeve between them. Specifically, the swaging rolls may have an incomplete circular shape, allowing them to be rotated to an inactive position in which position the active surfaces of the swaging rolls are directed outwards, away from each other, allowing free passage of a wire and a sleeve between an opening thus created between said rolls.

In another specific embodiment the attachment piece (16) is releasably connected to the pulling arrangement.

In yet another specific embodiment the pulling arrangement is a pulling arrangement including at least one hydraulic cylinder for providing a required pulling force.

According to second aspect the invention relates to a method of verifying the strain capacity of the attachment of the sleeve to the steel wire using an apparatus as described above. The method involves the steps of attaching the attachment piece of the apparatus to a coupling end of a sleeve that is attached to an end of a steel wire, fixing a portion of the steel wire in the holding unit of the apparatus, and pulling the sleeve attached to the wire held fixed in said holding unit and simultaneously monitoring a pulling force in order to verify said attachment.

Other embodiments and advantages will be apparent from the detailed description and the appended drawings.

BRIEF DESCRIPTION OF THE DRAWINGS

An exemplary embodiment related to the invention will now be described with reference to the appended drawings, in which.

DETAILED DESCRIPTION OF THE PREFERRED EMBODIMENTS

Figure 1:
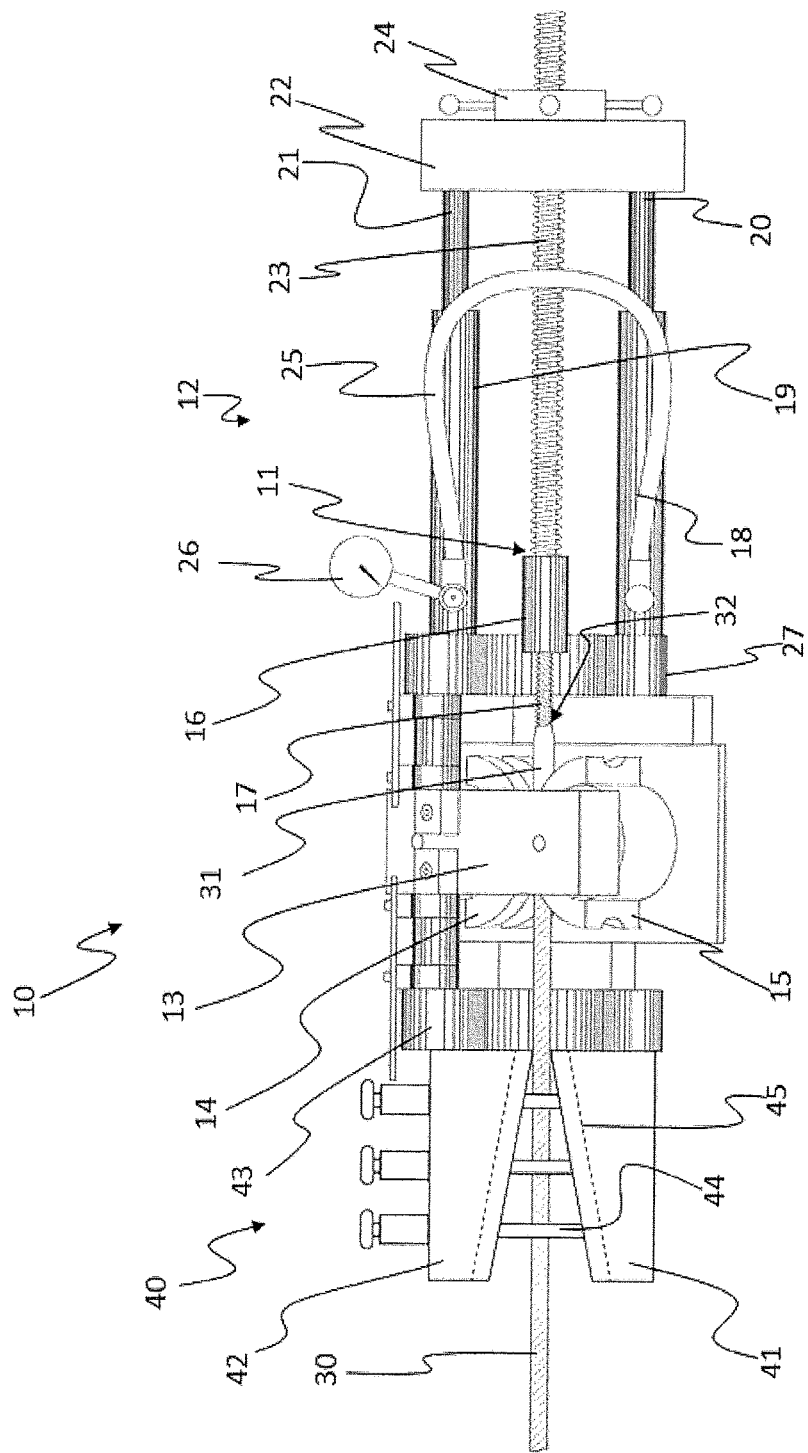
FIG. 1 shows a schematic embodiment of an apparatus in accordance with the invention, in operation of attaching a sleeve to a steel wire.

In FIG. 1 and apparatus 10 for attaching a sleeve 31 to a steel wire 30 by swaging is shown. The sleeve includes a coupling end 32 for facilitating handling of the steel wire 30. The apparatus comprises an attachment piece 16 arranged to connect to the coupling end 32 of the sleeve 31. A pulling arrangement 12 is connected to the attachment piece 16 via a pulling end 11.

In the shown embodiment the attachment piece 16 has a first end comprising a threaded bore for attachment to the pulling end 11, and a second opposed end comprising a screw 17 for insertion into the coupling end 32, in the form of a threaded bore, of the sleeve 31. Sleeves may have different shapes and different types of coupling ends 32 for attachment and therefore different attachment pieces may be needed in order to correctly connect to a specific sleeve. The attachment piece 16 should therefore be adapted to the specific coupling end 32 of the sleeve 31 that is to be attached to the steel wire 30. The coupling end 32 may, apart from a threaded bore, be a male thread, a claw, a loop, or the like, and the specific attachment piece used should be adapted to connect to the specific type of coupling end 32. The opposite end of the attachment piece is adapted to attach to the specific pulling end 11 of the pulling arrangement.

The pulling arrangement of the shown specific embodiment is a hydraulic arrangement and comprises two parallel hydraulic cylinders 18,19, arranged to control the extension of two parallel pistons 20,21 extending from the respective cylinders. A hydraulic hose 25 is arranged between the cylinders 18,19 to make sure that they are furnished with the same pressure, and a manometer 26 is arranged to monitor said pressure, and thereby the applied pulling force. The outer ends of the pistons are both attached to a block 22 to which a threaded pulling rod 23 comprising the pulling end 11 may be fixed. A safety nut 24 is arranged to lock the pulling rod 23 to the block 22. The locking is achieved by screwing the nut 24 tightly towards the block 22 so as to create a clamp force that locks the pulling rod 23 in a fixed position with respect to the block 22. The arrangement is flexible in that the pulling rod 23 has a substantial length the allows for a flexible positioning of the attachment piece 16 and sleeve 31 so as to allow correct positioning of the sleeve 31 with respect to the swaging rolls 14,15 of a cold rolling arrangement 13. The cylinders 18,19 are supported by a support structure 27 integrated in the apparatus 10, at one end of the apparatus.

Instead of a hydraulic arrangement the pulling arrangement may also be a electric pulling arrangement or a pulling arrangement driven by a combustion engine. A hydraulic arrangement is however advantageous in that it is size effective and may therefore be easily moved to location for operation on site.

The two mutually opposed swaging rolls 14,15 are adapted to swage, crimp or cold roll the sleeve 31 to a close press fit around a loose end of the steel wire 30. The swaging rolls are in the shown embodiment semi-circular. This is very much sufficient to press the full length of the sleeve 31 to be fastened to the steel wire 30. Often only about a quarter or a third of a lap of the swaging rolls are needed to press the full length of the sleeve 31. The apparatus 10 is adapted to swage sleeves of different sizes, typically matching steel wires of different sizes. Therefore, the swaging rolls are replaceable so that swaging rolls that match a specific size of a sleeve to be processed may be inserted into the cold rolling arrangement 13.

In a swaging process the sleeve 31 is swaged so as to attach to the end of the steel wire. This is achieved in that hydraulic fluid is pressed in to the hydraulic cylinders 18,19 so as to push the corresponding pistons 20,21 outwards and push the block 22 and the attached threaded rod 23 in a direction to pull the sleeve 31 and the wire 30 fitted inside it. As the sleeve advances, to the right in the figure, the swaging rolls 14,15 will roll with it so as to progressively swage the sleeve 31 into attachment with the end of the steel wire 30.

Figure 2:
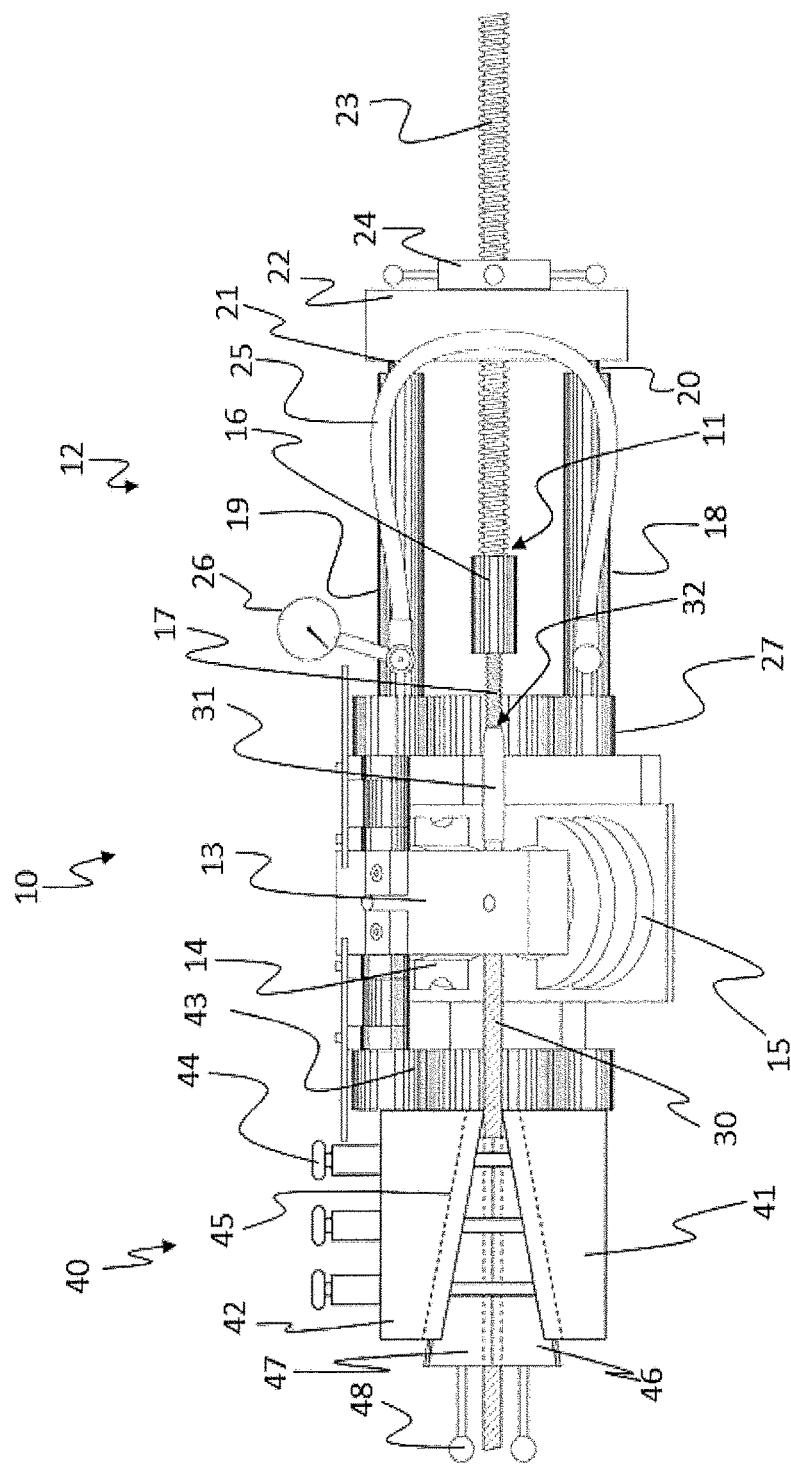
FIG. 2 shows the apparatus in FIG. 1 during testing of the strain capacity of the attachment between the steel wire and the sleeve.

The fact that the swaging rolls 14,15 are semi-circular as opposed to fully circular offers an advantage in that they may be turned to an inactive position, as illustrated in FIG. 2. In the inactive position the sleeve 31 and the steel wire 30 are free to move back and forth between them. This is advantageous because it allows the pulling arrangement to be used for other purposes.

Specifically, the apparatus 10 further comprises a testing arrangement for testing the strain capacity of the attachment between the sleeve 31 and the steel wire 30. The testing arrangement includes a holding unit 40 configured to effectively hold a portion of the steel wire 30 and allowing the pulling arrangement 12 to pull the sleeve 31, which is now attached to the wire 30, fixed in said holding unit 40.

In the shown embodiment the holding unit 40 comprises two opposed inclined support units 41,42. The support units are supported by a supportive end structure 43, which is an integrated part of the apparatus 10 and blocks the support units 41,42 from movement in the lengthwise direction of the steel wire 30. Further, the support units 41,42 are blocked from mutual movement away from each other by means of a blocking unit 44, which in the shown embodiment is comprised of six bolts, three on each side of a track 45 arranged along an axial centre line of the opposed support units 41,42. In the figures only the front three bolts are visible.

As is apparent from FIG. 2 these tracks 45 are arranged so as to allow insertion of wedges 46,47. The wedges may be provided with handles 48 for easy replacement. The wedges 46,47 comprise a lengthwise running recess adapted to a specific wire dimension and therefore several wedges of different dimensions are preferably available for use with a specific wire dimension. The wedges are produced of a strong material that may withstand the forces acting on it during operation but that preferably is softer than the steel wire so as to hold a steel wire without harming or leaving any marks on it. In one advantageous embodiment of the invention the wedges are provided in solid aluminium. Aluminium is advantageous as it is strong and ductile, so that it may withstand high pressure without being plastically deformed.

In order to make the wedges slide against the tracks of the support units, either the wedges, the tracks or both are preferably provided with a low friction material. It is important that the wedges will be able slide with respect the support units but not with respect to the steel wires. Therefore, the recesses for contact with the may be provided with friction enhancing portions, such as lateral ribs, dots or the like. The low friction material acting between the outside of the wedges and the tracks of the support units may be a layer of a plastic material, such as a polyamide, e.g. nylon. Preferably, said plastic material is arranged as a surface layer in the wedges.

The testing of the correct attachment of the sleeve 31 to the steel wire 30 is performed by positioning the wedges 46,47 in the tracks 45 of the opposed support units 41,42 and attaching the attachment piece 16 to the coupling end 32 of the sleeve 31. Of course, the pulling rod 23 should also be secured to the block 22. The testing is done by applying a force corresponding to a specific testing criteria by means of the pulling arrangement 12. The force is monitored by means of an indication means 26 for monitoring the traction force applied by the pulling arrangement 12. This monitoring may be done directly by a force meter or indirectly, i.e. by monitoring the hydraulic pressure by means of a manometer. For convenience, the scale of such manometer may be furnished with a scale indicating the pulling force corresponding to the reigning pressure. Otherwise, the force needs to be calculated or looked up in a table.

The testing apparatus is arranged to be used both directly following the attaching of a sleeve to a steel wire. Further though, testing may be performed on location on a steel wire-sleeve connection that has been in use. Such testing needs to be made at regular intervals and the present apparatus implies an apparent advantage with respect to conventional testing apparatuses, which in general are not mobile.

Above, the invention has been described with reference to a specific embodiment. It is obvious to a person skilled in the art that other embodiments are possible within the scope of the following claims.

The invention claimed is:

1. An apparatus for attaching and testing a sleeve to a steel wire, the sleeve having a coupling end, the apparatus comprising:
   an attachment piece arranged to connect to the coupling end of the sleeve to be attached to the steel wire,
   a pulling arrangement connected to the attachment piece and being configured to pull the sleeve via the connected attachment piece,
   a swaging arrangement including two opposed swaging rolls adapted to crimp the sleeve to a close press fit around a loose end of a steel wire,
wherein the apparatus further comprises a testing arrangement for verifying the strain capacity of the attachment of the sleeve to the steel wire by using the pulling arrangement to apply a pulling force to the sleeve attached to the wire and monitoring the force applied, the testing arrangement including: (i) a holding unit configured to effectively hold a portion of the steel wire fixed and allowing the pulling arrangement to pull the sleeve attached to the wire held fixed in said holding unit; and (ii) a manometer for monitoring a traction force applied by the pulling arrangement to the sleeve in order to verify said attachment.

2. The apparatus according to claim 1, wherein the holding unit comprises two opposed support units with inclined surfaces arranged to support two wedges for holding the steel wire fixed.

3. The apparatus according to claim 2, wherein the two wedges comprise tracks arranged to fit tightly around the steel wire to be fixed.

4. The apparatus according to claim 3, wherein the two wedges and/or the tracks of the support units are provided with a low friction surface layer.

5. The apparatus according to claim 4, wherein said low friction surface layer is comprised of a plastic material.

6. The apparatus according to claim 1, wherein the swaging rolls may be positioned in an inactive position so as to allow free passage of a wire and a sleeve between them.

7. The apparatus according to claim 6, wherein the swaging rolls have an incomplete circular shape, allowing them to be rotated to an inactive position in which position the active surfaces of the swaging rolls are directed outwards, away from each other, allowing free passage of the wire and the sleeve between an opening thus created between said rolls.

8. The apparatus according to claim 1, wherein the attachment piece is releasably connected to the pulling arrangement.

9. The apparatus according to claim 1, wherein the pulling arrangement is a hydraulic arrangement including at least one hydraulic cylinder for providing a required pulling force.

10. Method of verifying the strain capacity of the attachment of the sleeve to the steel wire using an apparatus according to claim 1, comprising the steps of:
    attaching a coupling end of a sleeve attached to an end of a steel wire to the attachment piece of the apparatus,
    fixing a portion of the steel wire in the holding unit of the apparatus, and
    pulling the sleeve attached to the wire held fixed in said holding unit and simultaneously monitoring a pulling force in order to verify said attachment.

* * * * *